(12) United States Patent
Känsäkoski et al.

(10) Patent No.: US 7,049,595 B2
(45) Date of Patent: May 23, 2006

(54) METHOD AND A MEASURING SYSTEM FOR DETERMINING AND MONITORING EXHAUST GAS EMISSION FROM A VEHICLE

(75) Inventors: Markku Känsäkoski, Oulu (FI); Pentti Niemelä, Jääli (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 319 days.

(21) Appl. No.: 10/474,434

(22) PCT Filed: Apr. 3, 2002

(86) PCT No.: PCT/FI02/00283

§ 371 (c)(1),
(2), (4) Date: Oct. 9, 2003

(87) PCT Pub. No.: WO02/082059

PCT Pub. Date: Oct. 17, 2002

(65) Prior Publication Data

US 2004/0104345 A1      Jun. 3, 2004

(30) Foreign Application Priority Data

Apr. 9, 2001    (FI) .................................. 20010729

(51) Int. Cl.
  *G01N 21/35*      (2006.01)
(52) U.S. Cl. .................................. 250/338.5

(58) Field of Classification Search .............. 250/338.5
See application file for complete search history.

(56) References Cited

U.S. PATENT DOCUMENTS

| | | | |
|---|---|---|---|
| 5,319,199 A | | 6/1994 | Stedman et al. |
| 5,498,872 A | | 3/1996 | Stedman et al. |
| 5,583,765 A | | 12/1996 | Kleehammer |
| 5,719,396 A | * | 2/1998 | Jack et al. .............. 250/338.5 |
| 5,726,450 A | | 3/1998 | Peterson et al. |
| 5,831,267 A | | 11/1998 | Jack et al. |
| 5,877,862 A | | 3/1999 | Nelson et al. |

FOREIGN PATENT DOCUMENTS

WO          00/26641 A1      5/2000

* cited by examiner

*Primary Examiner*—Constantine Hannaher
(74) *Attorney, Agent, or Firm*—Venable LLP; Eric J. Franklin (57) ABSTRACT

A method and a measuring system for determining exhaust gas emissions from a moving vehicle by a remote optical measuring technique. The model and/or type of the vehicle under examination is identified, and the driving situation of the vehicle in question is determined at the moment of measurement. A calculatory vehicle model is used to determine a case-specific estimate for the carbon dioxide concentration of the exhaust gas plume depending on the vehicle in question and its driving situation. The accuracy of determining the concentrations of the actual emission gases is improved by eliminating the inaccuracy of the carbon dioxide concentration values.

31 Claims, 6 Drawing Sheets

METHOD AND A MEASURING SYSTEM FOR DETERMINING AND MONITORING EXHAUST GAS EMISSION FROM A VEHICLE

CROSS-REFERENCE TO RELATED APPLICATION

This application claims priority from Finnish patent application 20010729 filed 9 Apr. 2001 and is the national phase of PCT/FI02/00283 filed 3 Apr. 2002.

FIELD OF THE INVENTION

The invention relates to a method for determining and monitoring exhaust gas emissions from a moving vehicle or a corresponding object by remote measuring techniques. The invention also relates to a measuring system for implementing the afore-mentioned method.

BACKGROUND OF THE INVENTION

Exhaust gas emissions from traffic, particularly road traffic, constitute a significant part of harmful emissions caused by human activity to the environment. For example in 1998, exhaust gas emissions from traffic made up about 50% of all emissions caused by the combustion of fossil fuels to the environment in Finland.

Certain upper limits are set by legislation for harmful exhaust gas emissions of vehicles used in road traffic, such as for the emissions of carbon monoxide (CO), hydrocarbons (HC), nitrogen oxides ($NO_x$) and fine particles. These limit values may vary according to the vehicle (type of vehicle and engine, age of vehicle) and, to some extent, also according to the country. The trend is to continuously and gradually reduce said limit values as well as to bring them to a uniform international level. Authorities setting limit values for exhaust gas emissions include, for example, the Commission of the European Union and the United States Environmental Protection Agency (US-EPA).

According to regulations addressed directly to vehicle manufacturers, new vehicles entering the market must fulfil the criteria for exhaust gas emissions which are valid at the time. The meeting of said criteria is controlled by means of various type approval tests. The type approval tests include, for example, the measurement of exhaust gases during a specific simulated test period including accelerations, decelerations and stops when the vehicle is driven in a dynamometer. However, the type approval tests are only made for a number of vehicles before the approval of said vehicle type/model for sale and use, wherein they can naturally not be used to monitor the condition of vehicles which have already been taken into use.

Of vehicles in actual use in road traffic, significant differences can be found in exhaust gas emissions between different vehicles, due to e.g. the condition and/or age of the vehicles. Older vehicles and/or vehicles in poorer condition cause considerably higher emissions than newer vehicles which are technically more developed and in good condition. Therefore, it can be stated that as the engine technology of vehicles and the technology in the reduction of exhaust gases are developed further and as the vehicle stock is simultaneously renewed, fewer and fewer old vehicles and/or vehicles in poor condition will cause a significant part of all emissions caused by vehicles. Investigators in the field have presented estimates that for example at present, about 10% of the vehicles cause about 50% of the CO emissions from all the vehicles.

By reason of what has been presented above, the authorities should control the observation of statutory limit values also vehicle by vehicle when the vehicles are already in use in road traffic. Typically, such a control is made in connection with the statutory inspections of vehicles at regular intervals. In an inspection situation, as well as in maintenance, exhaust gas emissions are typically measured during idle running or fast idle running, without substantially loading the engine. Consequently, this measuring method does not correspond to the normal use of the vehicle in road traffic, with a varying load on the engine. Moreover, in several countries, for example in Finland, regular annual inspections of vehicles are only started after several years of the introduction of a new vehicle. Therefore, the vehicle may, even before the first inspection or during the interval between the annual inspections, cause emissions which exceed the limit values but which are not detected by the authorities.

Consequently, new measuring and monitoring methods are needed to monitor efficiently the exhaust gas emissions of single vehicles in a situation corresponding to their normal use and irrespective of inspection times or other predetermined times of testing. Various solutions are known from prior art to use road-side measurement stations to determine emissions caused by single vehicles passing the measurement station, by remote measuring techniques directly when the vehicles are moving.

U.S. Pat. No. 5,498,872 (Stedman et al.) presents a solution for the remote measurement of exhaust gases from a moving vehicle. In this method, infrared (IR) and ultraviolet (UV) radiation is directed through an exhaust gas plume emitted by a vehicle after the vehicle has passed the measurement station. Means for emitting and detecting IR and UV radiation of the measurement station are placed on different sides of the lane along the road. The concentrations of said exhaust gases are determined on the basis of the absorption caused by the exhaust gases contained in the emissions at the wavelength band specific to each component. The measurement of CO and HC concentrations is based on the absorption in the IR range, and the NO concentration is measured by means of the absorption in the UV range.

U.S. Pat. No. 5,831,267 (Jack et al.) presents a method which largely corresponds to said U.S. Pat. No. 5,498,872 but in which the measurement of the NO concentration is implemented in the IR range, wherein the apparatus becomes simpler, because a separate light source in the UV range will thus not be needed.

In view of the present invention, said U.S. Pat. No. 5,831,267 (Jack et al.) can be considered to represent the closest prior art.

The measurement of exhaust gas emissions by the above-mentioned methods based on the absorption in the measuring beam is a demanding task, because one of the most important basic principles of absorption spectroscopy is not fulfilled: the exact length of absorption range is not known, because the precise shape of the exhaust gas plume is not known and also the shape of the exhaust gas plume will vary quickly in time by the effect of e.g. turbulence and wind, as the concentrations of the exhaust gas plume are simultaneously diluted.

The use of absorption spectroscopy in measurements of gas concentration is based on the known law of Lambert and Beer:

$$I(\lambda) = I_0(\lambda) e^{-k(\lambda)x} \qquad (1)$$

In Formula 1, $I(\lambda)$ is the intensity of a measuring beam which has passed the gas layer to be measured in an absorption length x, and $I_0(\lambda)$ is the original intensity of the measuring beam before the absorption caused by the gas layer. The factor $k(\lambda)[1/m]$ is an absorption coefficient which depends on the effective absorption cross-section $Q(\lambda)[m^2]$ as well as on the gas concentration N $[1/m^3]$ according to Formula 2.

$$k(\lambda) = Q(\lambda)N \quad (2)$$

In a situation, in which the effective absorption cross-section $Q(\lambda)$ and the absorption length x of the gas are known, it is possible to determine the gas concentration N by means of the ratio $I/I_0$. The effective absorption cross-section $Q(\lambda)$ can be determined by calibration measurements made in advance, and/or its value for the gas in question can be found out in prior art.

Below, the term transmission will be used for the ratio $I/I_0$, which may thus receive values between zero and one.

In the above-mentioned solutions of prior art, Stedman et al. and Jack et al. base their measurements on the presumption that the distributions and dilutions of $CO_2$ and the other emission gases CO, HC, $NO_x$ contained in the exhaust gas are similar. Thus, by measuring the transmission of the actual emission gases CO, HC, $NO_x$ and simultaneously the transmission of $CO_2$ in the IR range, it is possible to determine, with high precision, the concentration of each emission gas in relation to the concentration of $CO_2$.

Furthermore, Stedman et al. and Jack et al. presume that the concentration of $CO_2$ in the exhaust gas is known and substantially constant (independent of the driving situation), wherein by means of the constant concentration determined for $CO_2$ it is also possible to determine the absolute concentrations of the other measured emission gases by means of the transmissions proportioned to the transmission of $CO_2$.

To determine the concentration of $CO_2$ in the exhaust gas required in said method, Stedman et al. and Jack et al. solve the stoichiometric combustion equations. However, this approach involves a number of various problems.

The first problem is that, to solve the combustion equations, it is necessary to make presuppositions about the ratios between hydrogen and carbon contained in the fuel and in the exhaust gases. Stedman et al. suppose that the ratio between hydrogen and carbon in both is 2:1. Jack et al. suppose that the ratio is 1.85:1 in fuel and 2.33:1 in exhaust gas. Although the presupposition of Jack et al. is more realistic, it does not take into account fuels with different compositions, such as for example petrol and diesel oil, and thereby the different compositions of the exhaust gases.

Another problem of this approach is that the combustion in the engines does not, by any means, always take place stoichiometrically. Nonstoichiometric combustion may occur in petrol engines for example in situations in which the engine and/or the fuel supply is defective, or they have been intentionally modified, for example for a higher power output. Petrol engines may thus operate with a too rich or too thin mixture with respect to a stoichiometric mixture of fuel and air. Because of their operating principle, diesel engines also normally operate with an excess of air; in other words, there is always an excess of air in relation to the fuel in the cylinder with respect to the concentration required for stoichiometric combustion.

The third problem is that the above-mentioned approach completely disregards chemical reactions taking place in a catalytic converter which is possibly used in the vehicle to change the composition of the exhaust gas.

The above description can thus be summarized by stating that to determine the absolute concentration of $CO_2$ in exhaust gases, it will not be sufficient to solve the stoichiometric combustion equations in general, which will give, as the result, a constant value for the concentration of $CO_2$ in the exhaust gases, irrespective of the driving situation. If the $CO_2$ concentration determined in this way is used further to determine other emission gases by proportioning the transmissions measured for them with the transmission of $CO_2$, inaccuracies will also be caused in the determination of the concentrations of said other emission gases.

U.S. Pat. No. 5,583,765 (Kleehammer) presents a remote measuring technique intended particularly for heavy vehicles, to determine the total weight and exhaust gas emissions of a single vehicle, such as a trailer lorry, within allowed limit values. The measurement apparatus, which is preferably set up by the side of a road in a region where there is an upgrade, makes it possible to collect following information about a single vehicle and the measurement situation/site:

- model/type data of the vehicle (dead weight, engine type, transmission properties) for example by means of a bar code sign placed in the vehicle for this purpose,
- speed of the vehicle for example by means of a radar speedmeter,
- ambient conditions at the measurement site, such as for example air temperature, wind velocity, relative humidity, and air pressure,
- temperature of the exhaust gas plume for example by means of an IR camera,
- upslope of the road (gradient of the ascent) at the measurement site,
- chemical composition of the exhaust gas plume measured by spectroscopy,
- registration data of the vehicle, for example, by automatically identifying the numbers on the registration plate from an image which is taken of the vehicle.

The method of Kleehammer is essentially based on the presupposition that the temperature of the exhaust gas plume correlates with the power output of the engine. In other words, the higher the power output of the engine, the higher the temperature of the exhaust gas plume. In the method, the vehicle is identified, and the speed of the vehicle and the temperature of the exhaust gas plume are determined when the vehicle is driven uphill, wherein said speed and temperature can be used to obtain information about the power output of the engine of the vehicle. This information can further be used to determine the total weight and load of the vehicle when the properties of the vehicle type in question (dead weight, engine type, power train), the slope of the hill and the other ambient conditions (air temperature, wind velocity, relative humidity, air pressure) are known.

In the method of Kleehammer, the chemical composition of the exhaust gas plume is also measured spectroscopically. Further, this measured profile of the exhaust gas emissions is compared with a reference profile which can be determined when the vehicle type and the power output of its engine in the measuring situation are known. In U.S. Pat. No. 5,583,765, Kleehammer briefly mentions (e.g. column 5, line 60 to column 6, line 4) that the reference profiles of exhaust gas emissions can be based, for example, on the limit values for the vehicle type in question, or on measurement data produced for the vehicle type by vehicle manufacturers or independent testing agencies. Furthermore, in U.S. Pat. No. 5,583,765, Kleehammer does not describe in more detail, how the spectroscopic measurement of the chemical composition of the exhaust gas emissions is implemented.

In view of the present invention, it is essential that the measurement of the profile of exhaust gas emissions and the determination of the reference profile according to the Kleehammer method as presented in U.S. Pat. No. 5,583,765 are carried out as completely separate operations and the profiles produced by them are only compared with each other to determine, whether the exhaust gas emissions (measured profile) of the vehicle in question fall within the allowed limits. The information contained in the reference profile is not utilized in any way to improve the accuracy of the measuring result.

As the Kleehammer method is substantially based on the presupposition that the temperature of the exhaust gas plume correlates with the power output of the engine, the method is primarily suitable for heavy diesel-engined vehicles only, which discharge an exhaust gas plume that is sufficiently large and hot for accurate measurement of the temperature of the exhaust gases. In vehicles equipped with a catalytic converter, such as petrol-driven cars, the temperature of exhaust gases discharged from the exhaust pipe into the air does not correspond directly to the power output of the engine any longer but is primarily dependent on the operating temperature of the catalytic converter itself.

The primary aim of the present invention is to provide a new method for determining and controlling exhaust gas emissions from a moving vehicle or a corresponding object by a remote measuring technique, which method makes it possible to measure the absolute concentrations of emission gases contained in the exhaust gas plume with a significantly higher precision than in solutions of prior art.

It is also an aim of the invention to provide a measuring system implementing the aforementioned method.

In the solution according to the invention, the vehicle under examination and its model/type are identified, and further, the driving situation of the vehicle is determined. Thus, by means of modeling, it is possible to determine the exhaust gas emissions, and particularly the calculatory $CO_2$ concentration of the exhaust gases, from the vehicle, particularly in the driving situation in question.

The basic idea of the invention is that no predetermined constant value is presupposed for the $CO_2$ concentration of the exhaust gases, but the estimate for the $CO_2$ concentration to be determined for the vehicle by calculation may vary according to the vehicle in question and the driving situation at the moment of measurement.

The calculatory value for the $CO_2$ concentration, determined in this way and being more precise than in prior art, further makes it possible to determine the actual harmful emission gases, such as CO, HC, NO, more precisely by absorption spectroscopy and by proportioning the transmissions measured for said other emission gases with the transmission of $CO_2$. In other words, the method according to the invention solves the problem caused by the fact that the precise absorption length and/or the precise shape of the exhaust gas plume and/or the dilution of the exhaust gases are not known. When the absolute concentration of $CO_2$ is known, it is possible to determine, on the basis of the optical transmission measured for $CO_2$, the so-called effective absorption length which is the same for all the emission gases and which can thus be used to determine the absolute concentrations of the emission gases by means of the optical transmissions measured for them.

In an advantageous embodiment of the invention, the optical absorptions caused by all the emission gases to be examined, as well as by $CO_2$ which is used as an indicator, are measured by measuring all said gases substantially at the same point in the exhaust gas plume and also by storing the measuring signals substantially at the same time. This will improve the accuracy of the measurement, because the composition and shape of the exhaust gas plume will thus be the same for all the gases to be measured.

In an advantageous embodiment of the invention, also the NO measurement is performed in the IR range, wherein the measuring system becomes simpler, because there will thus be no need for a separate illuminator in the UV range, optics and a detector. A known problem with NO measurement in the IR range is the strong absorption spectrum of water vapour falling in the same wavelength range and tending to interfere with the NO measurement. According to the invention, this problem is avoided by performing the NO measurement in the IR range by using a so-called correlation technique using an optical filter or filter arrangement as a wavelength filter in the reference and/or measuring channel, wherein the transmission as a function of the wavelength correlates with the comb-like structure of the spectral lines of the absorption spectrum in the neighbourhood of 5.25 μm of NO. Because of better selectivity which is thus achieved in the optical measurement, the effect of water vapour on the result of the NO measurement is thus effectively minimized, and the sensitivity and accuracy of the measurement are improved. Preferably, said filter means used is either a Fabry-Perot comb filter or a so-called NO gas cell filter.

The most important advantages of the present invention include a significant improvement in the accuracy of the measurement of emission gases when compared with solutions of prior art. This makes it possible to classify vehicles, for which the measurements have been taken, as passing or violating the criteria set for exhaust gas emissions, with a smaller margin or error.

The invention improves the accuracy of measurement particularly for vehicles equipped with a catalytic converter and for diesel vehicles.

Furthermore, since the model and state of motion of the vehicle in the measuring situation and under the measuring conditions are known according to the invention, it is possible to use a calculatory vehicle model to determine the real fuel consumption of the vehicle at the moment of measurement, wherein it is further possible to determine the coefficients of emissions of harmful gases for the vehicle, in the form of g/km (and/or g/s and/or g/kWh). The emission coefficients obtainable in this form can be used to evaluate the total emissions caused by the vehicles, and they make it possible to make a direct comparison, for example, with results relating to the quality of air in urban areas. If the fuel consumption of the vehicle is not known, then it is not possible to convert the emission gas concentrations obtained by the absorption measurement to said emission coefficients in a realiable manner.

The following more detailed description of the invention to be explicated with examples will more clearly illustrate, for anyone skilled in the art, advantageous embodiments of the invention as well as advantages to be achieved with the invention in relation to prior art.

BRIEF DESCRIPTION OF DRAWINGS

In the following, the invention will be described in more detail with reference to the appended drawings, in which.

The appended drawings are only intended to illustrate the invention, and thus the structures and components shown in them are not drawn to correspond to their dimensions in reality. For the sake of clarity, the figures do not show components and/or functions which are irrelevant and obvious for anyone skilled in the art as such.

DETAILED DESCRIPTION OF EMBODIMENTS OF THE INVENTION

The Measuring System and the Information Collected By It

Figure 1:
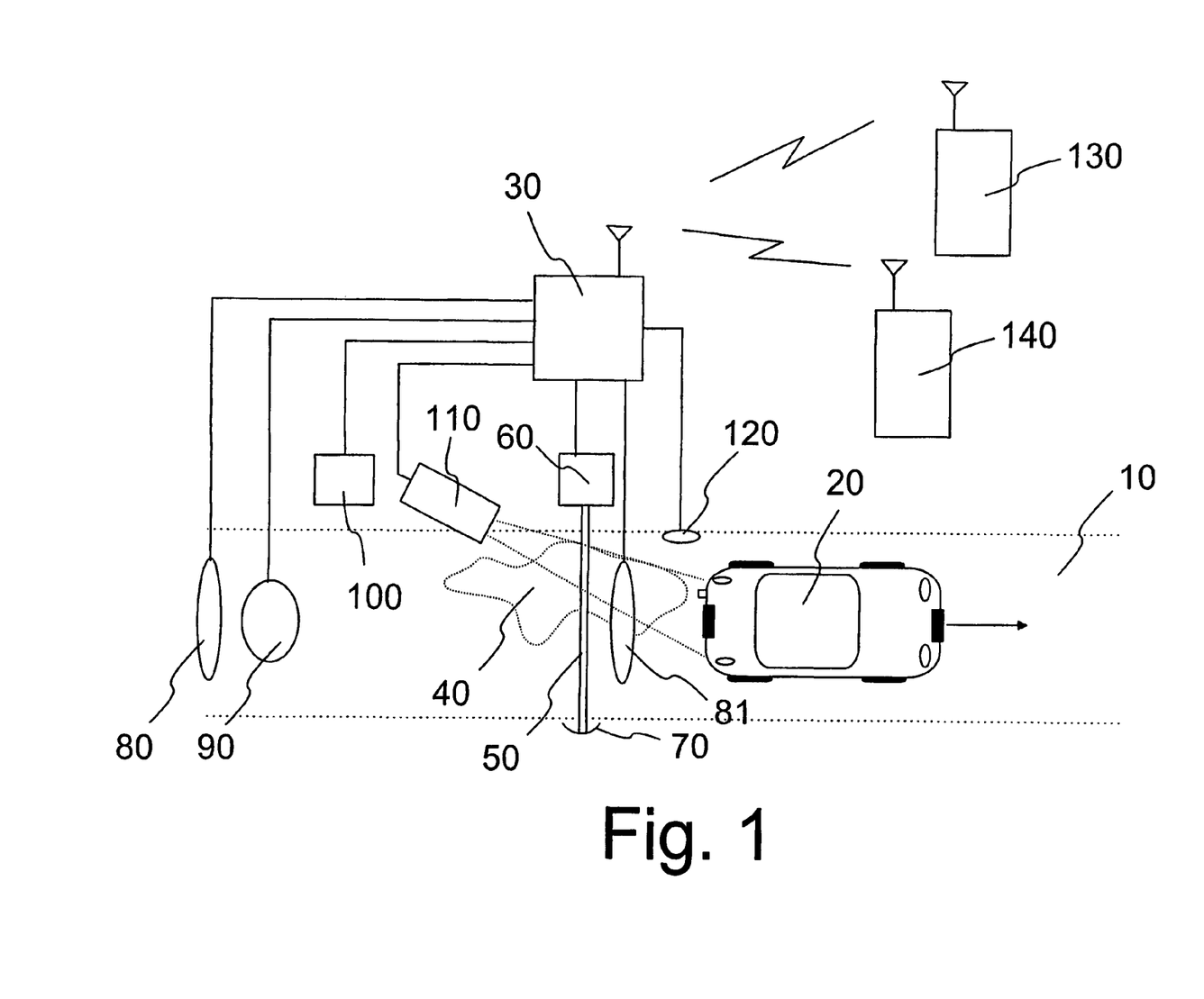
FIG. 1 shows, in principle, a measuring system according to the invention.

FIG. 1 shows, in principle, the essential elements of a measuring system according to the invention. The measuring system, which may be of a type placed stationary in its position or of a movable type, can comprise means and functions for storing following information about a vehicle 20 moving along a road 10 in a data processing unit 30.

1) Means 60 for determining the optical absorption caused by the gases CO, HC, NO, $CO_2$ contained in an exhaust gas plume 40 in a measuring beam 50 on a wavelength band specific to each of said gases. Said measurement is preferably made by means of a spectrometer 60 placed along the road 10, the spectrometer 60 comprising an illuminator emitting IR radiation as well as optics for directing the radiation emitted by said illuminator in a substantially collimated measuring beam 50 to a reflector 70 placed on the opposite side of the road 10. The reflector 70 will reflect the measuring beam 50 along substantially the same route back to the spectrometer 60, in which the measuring beam 50 is detected in a spectrally resolved way.

2) Means 80, 81 for measuring the speed and acceleration of the vehicle 20. Preferably, said means comprise induction loops 80, 81 installed at regular intervals in the carriageway of the road 10. The speed of the vehicle can be determined in a known way by utilizing the time difference between the signals generated by the front part and the back part of the vehicle in one induction loop. By measuring the speed of the vehicle in the above-mentioned way at two locations with two different induction loops, it is possible to find out the acceleration of the vehicle. The information measured in the above-mentioned way can also be utilized for classifying the vehicle as a light vehicle (e.g. a car) or a heavy vehicle (e.g. a trailer lorry). Naturally, it is obvious that the acceleration of the vehicle can also be determined by another way obvious for anyone skilled in the art, such as by a radar speed-meter based on radio waves or laser light.

3) Means 90 for determining the total weight of the vehicle 1. Preferably, said means 90 comprise a piezo sensor or sensors installed in the carriageway of the road 10. The information measured in the above-mentioned way can also be utilized to classify the vehicle as a light vehicle or a heavy vehicle.

4) Means 100 for determining ambient conditions at the measurement site, such as the air temperature, wind velocity, relative humidity, and air pressure.

5) Means 110 for identifying the vehicle 20. Preferably, said means 110 comprise a device for reading the registration plate on the basis of a machine vision system.

6) A function/means 120 for determining the profile (flat/slope) and the roughness of the surface of the road 10 in the driving direction. Preferably, the profile of the road 10 in the driving direction is determined by the person installing the measuring system, wherein said information, which remains substantially constant, is simultaneously input in the data processing unit 30. When the roughness of the surface of the road 10 is changed, for example, because of snow or ice, the system may, if necessary, be connected to functions based on machine vision, or the like, to update the roughness data in the data processing unit 30.

The data processing unit 30 of the measuring system comprises software for collecting said information from said means, as well as for processing and storing said information. Furthermore, the data processing unit 30 can be in a data transmission connection with one or more external systems for obtaining additional information and/or function commands, and/or for transmitting measurement data and/or data relating to the functional status of the measuring system further.

From an external database (databases) 130, the data processing unit 30 receives the model/type data of the vehicle 20 (dead weight, engine type, transmission properties) on the basis of the data on the registration plate of the vehicle 20. Preferably on the basis of the data on the registration plate of the vehicle 20, information is first retrieved from a so-called register database about the exact type and/or model of the vehicle, and then, by means of this type and/or model data, the more exact properties of the vehicle type in question are found out from a so-called type database.

Preferably, the data processing unit 30 is also connected to a data system 140 of the agency maintaining the measuring system, from which the measuring system receives function commands and to which the measuring system can transmit messages relating to its own state, such as notices of defects. To said external data system 140, the data processing unit 30 can transmit statistical measuring data and/or measuring data relating to single vehicles, which the data system 140 can transmit further to authorities or the like.

The Most Important Functions of the Measuring System

Figure 2:
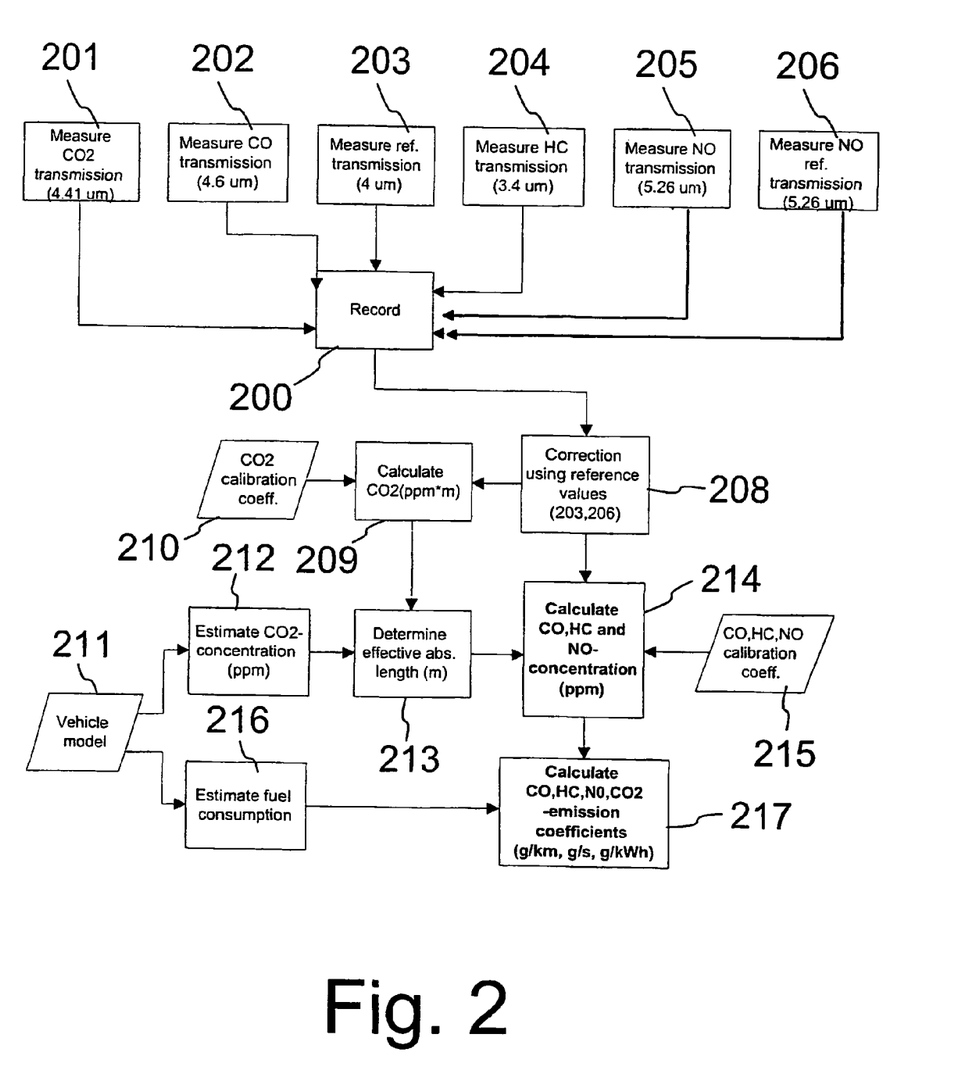
FIG. 2 shows, in flow charts, an embodiment of the method according to the invention.

FIG. 2 shows, in flow charts, an embodiment of the method according to the invention. The functions shown in FIG. 2 can be arranged to be performed wholly in the data processing unit 30 or, for applicable parts, also in external data systems 130, 140, to which the data processing unit 30 is connected.

In blocks 201, 202, 204, and 205 of the flow chart, the spectrometer 60 measures the transmission of radiation in the IR range which has passed in a measuring beam 50 through an exhaust gas plume 40 at the different absorption wavelength bands specific to the gases $CO_2$, CO, HC, NO, wherein some possible average wavelengths are indicated in the block corresponding to each gas in FIG. 2. As it will be obvious for anyone skilled in the art, the transmission measurement takes into account, if necessary, the properties of the different components (illuminator, detectors, optics) of the spectrometer 60 as well as the properties of the reflector 70 which are changed as a function of the wavelength. These so-called device functions can be stored in advance, for example in the form of calibration curves, in the memory of either the spectrometer 70 or the data processing unit 30.

Furthermore, reference transmissions are separately measured for $CO_2$, CO and HC at about 4 micrometres in block 203, and for NO at about 5.26 micrometres in block 206.

Advantageously, the same common reference wavelength can be used for $CO_2$, CO and HC (block 203), because the absorption wavelengths of these gas components are located sufficiently close to each other. Because the reference measurement in block 203 is not made at the absorption wavelength of any given gas component, the measuring wavelength may differ to some extent from the 4 micrometres shown in FIG. 2. The wavelength of the reference measurement can be selected to be suitable, for example in the range of 3.8 to 4 micrometres. It will be obvious for anyone skilled in the art that it is also possible to use reference measurements at several wavelengths, if necessary.

Except for the measurements related to NO in blocks 205 and 206, the above-described measurements of the optical transmission of the gases $CO_2$, CO and HC (blocks 201, 202 and 204) and the reference (block 203) can be made by any method and/or optical arrangement which will be obvious as such for a person skilled in the art.

For NO, the reference measurement is made separately at 5.26 micrometres in block 206, particularly to minimize the influence of water vapour contained in the air and/or in the exhaust gas plume 40, as well as to improve the sensitivity of the measurement. This will be described more closely below in connection with the more detailed description of the NO measurement according to the invention.

In block 200, the transmission signals recorded in the above-mentioned way substantially at the same time and at the same point in the exhaust gas plume 40 for the different gas components $CO_2$, CO, HC, NO and their references are stored in the data processing unit 30.

If necessary, the attenuation caused in the measuring beam 50 by impurities or the like in ambient air and/or in the exhaust gas plume 40 is corrected in the transmissions measured in block 208 of FIG. 2. Such impurities include, for example, particles of dust or carbon black. Also other gas components as well as water vapour may cause undesirable absorption at the measuring wavelength of the gas component under investigation. The correction is made, in practice, by computing the ratio between the transmission under investigation and the reference transmission. For $CO_2$, CO and HC, this is performed by means of the reference signal measured in block 203, and for NO, in turn, by means of the reference signal measured in block 206. In the case of NO, said correction will efficiently include also the attenuation caused by water vapour in the measuring beam 50.

After the correction made in block 208 of FIG. 2, the real transmission values ($I/I_0$, see Formula 1) are available for each gas $CO_2$, CO, NC, NO. These transmission values substantially indicate only the absorptions caused by the exhaust gas plume 40 in the measuring beam 50 at wavelength bands corresponding to said gases.

In block 209 of FIG. 2, the transmission value determined for $CO_2$ in the above-mentioned way is converted, for example by calibration factors predetermined under laboratory conditions (block 210), to be indicated as a value according to the unit concentration×absorption length (ppm×m).

The input data for the vehicle model in block 211 (vehicle model/type and properties, speed, acceleration and weight of the vehicle, weather and ambient conditions at the measurement site and in the measuring situation) are used to determine a calculatory value for the absolute $CO_2$ concentration in the exhaust gases of the vehicle in block 212. By combining, in block 213, the absolute $CO_2$ concentration (ppm) obtained from the vehicle model and the measured value (ppm×m) determined for $CO_2$, it is possible, by means of the $CO_2$ and according to the invention, to determine the effective absorption length of the measuring beam 50 in the exhaust gas plume 40.

After this, in block 214, by combining the data about said effective absorption length and the calibration factors predetermined for the emission gases CO, HC, NO for example under laboratory conditions (block 215), it is possible to compute the absolute values for said emission gases as ppm values or the like.

Furthermore, an estimate for the fuel consumption of the vehicle at the moment of measuring (block 216) is obtained from the vehicle model (block 211). By combining the data about the momentary fuel consumption of the vehicle and the composition of the exhaust gas plume 40 of the vehicle, it is possible, in block 217, further to determine the emission factors for each gas (CO, HC, NO, $CO_2$) contained in the exhaust gases of the vehicle, as values of emission gas mass per distance driven (g/km) and/or as emission gas mass per unit of time (g/s) and/or as emission gas mass per engine output (g/kWh).

Furthermore, the data processing unit 30 can compare the emission profile (CO, HC, NO) measured in the above-identified way according to the invention with the allowed limit values and, if necessary, transmit the data to the authorities, or the like, controlling the matter.

The General Structure of the Spectrometer

Figure 3:
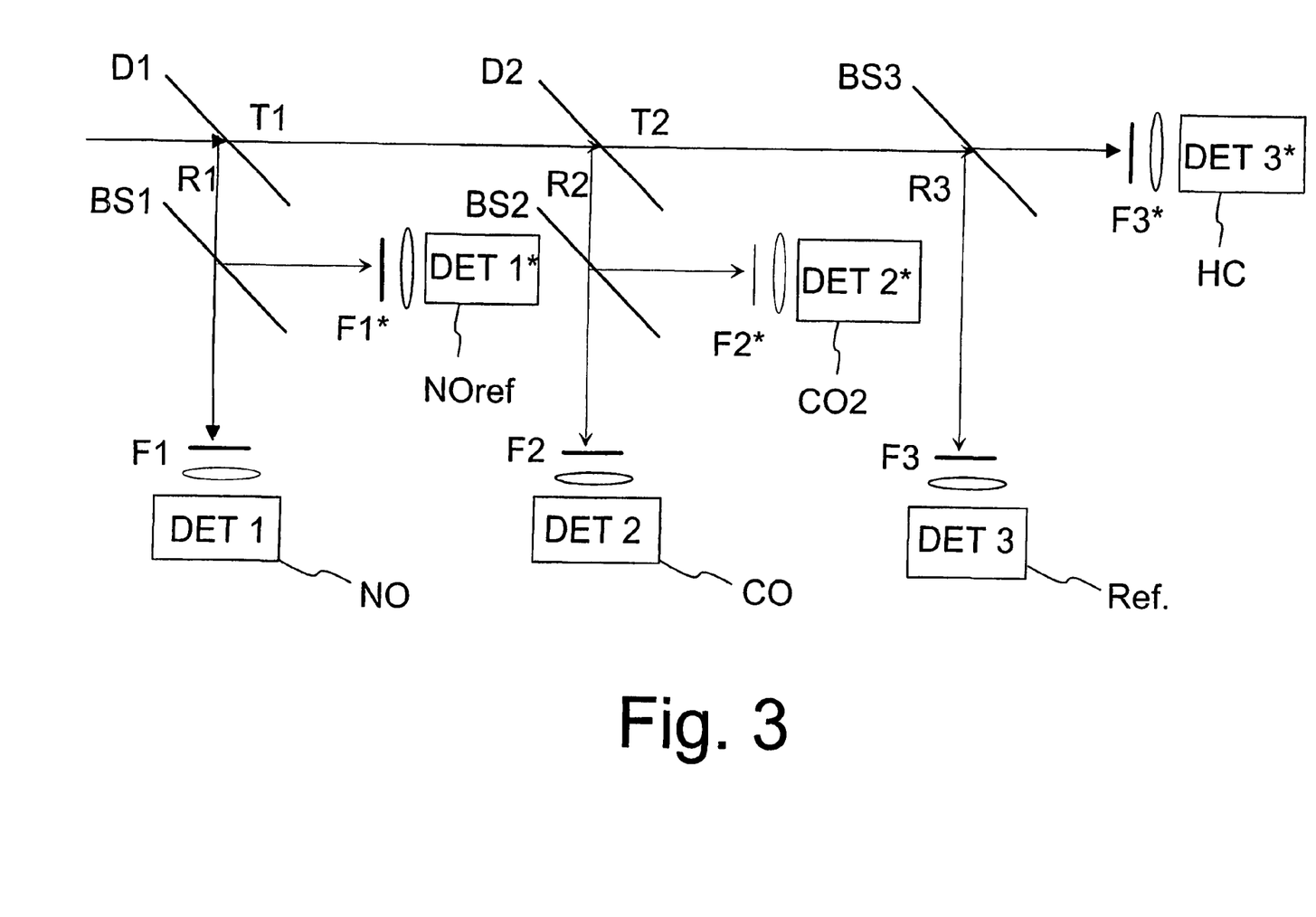
FIG. 3 shows, in principle, an optical arrangement in the detector section of a spectrometer according to the invention.

FIG. 3 shows, in principle, one possible optical arrangement for the detector section of a spectrometer 60.

The measuring beam 50, entering from the left in FIG. 3, is divided into detectors DET1, DET1*, DET2, DET2*, DET3, DET3* by means of dichroic mirrors D1, D2 and beam splitters BS1, BS2, BS3. In front of each of said detectors, a filter F1, F1*, F2, F2*, F3, F3* is used, to cut out the radiation allowed to enter said detector more precisely.

Table 1 shows the properties of the essential components of the spectrometer according to FIG. 3.

The IR light source included in the spectrometer 60 is preferably for example an infrared filament, a so-called globar or silicon carbide bar. These IR light sources emit radiation substantially according to Planck's law of radiation, i.e. they act in the way of a so-called black body. As the IR light source, it is also possible to use any other solution obvious for a person skilled in the art, including non-thermal radiators, such as LED's of the infrared range.

TABLE 1

Properties of essential components of the detector section in the spectrometer 60 according to FIG. 3.

| | | |
|---|---|---|
| D1 | dichroic 45° mirror | reflects 5–5.5 µm (R1), transmits 3–4.8 µm (T1) |
| D2 | dichroic 45° mirror | reflects 4.3–4.8 µm (R1), transmits 3–4.2 µm (T1) |

TABLE 1-continued

Properties of essential components of the detector section in the spectrometer 60 according to FIG. 3.

| | | |
|---|---|---|
| BS1-BS3 | beam splitter | splitting ratio 50/50, irrespective of wavelength |
| F1 | filter of NO measurement band | band pass filter (FIG. 7) or band pass filter + Fabry-Perot (FIG. 8) - center wavelength of pass band 5.26 μm |
| F1* | filter of NO reference band | band pass filter + NO filter cell (FIG. 7) or band pass filter + Fabry-Perot (FIG. 8) - center wavelength of pass band 5.26 μm |
| F2 | filter of CO measurement band | band pass filter - center wavelength of pass band 4.6 μm |
| F2* | filter of $CO_2$ measurement band | band pass filter - center wavelength of pass band 4.41 μm |
| F3 | filter of reference band (CO, $CO_2$, HC) | band pass filter - center wavelength of pass band about 4.0 μm |
| F3* | filter of HCO measurement band | band pass filter - center wavelength of pass band 3.4 μm |

As the detectors DET1, DET1*, DET2, DET2*, DET3, DET3* in the spectrometer 60, it is possible to use, for example, PbSe detectors or MCT (Mercury Cadmium Telluride) detectors. The last mentioned ones are particularly suitable for measurements at a wavelength exceeding 5 μm.

To detect IR radiation, it is advantageous to modulate the radiation emitted by the IR light source, for example, by a mechanical chopper, electrical optical modulator placed in front of the IR light source, or by alternating the electrical power to be supplied to the IR light source. By detecting the signal of the detectors DET1, DET1*, DET2, DET2*, DET3, DET3* at a narrow electrical pass band corresponding to the frequency of said modulation, it is possible, in a way known as such, to filter from the signals the background signals of other possible IR radiation sources in the visual field of the detector element, such as those caused by the exhaust gas plume itself or other background. The detection can be performed in ways known as such by using, for example, a so-called lock-in amplifier, phase-sensitive detection or an adapted filter.

It should be noted that except for the measurement of the NO transmission and reference signals according to the invention, based on correlation techniques, i.e. for example Fabry-Perot comb filters or a NO gas cell filter (blocks 205 and 206 in FIG. 2), the spectrometer 60 can also be implemented in any other way obvious for a person skilled in the art.

Naturally, it will be obvious for a person skilled in the art that the desired wavelength bands for the detectors DET1, DET1*, DET2, DET2*, DET3, DET3* can also be arranged in other ways than by the optical arrangement shown in FIG. 3. For example, by directing the measuring beam 50 entering the detector section to pass through dichroic mirrors placed one after the other on the optical axis of the measuring beam 50, at an angle of 45 degrees to the measuring beam 50, it is possible to use each dichroic mirror to separate the necessary wavelength bands directly to the detectors DET1, DET1*, DET2, DET2*, DET3, DET3* without using separate band pass filters. This solution is advantageous for maximizing the optical signal, but it requires the use of dichroic mirrors whose wavelength bands are implemented particularly for this purpose.

Furthermore, the measurements of the optical transmissions of the gases $CO_2$, CO and HC (blocks 201, 202 and 204 in FIG. 2) and the reference (block 203 in FIG. 2) by the spectrometer 60 can also be implemented in other ways than the above-described ways based on the use of mirrors and band pass filters. The differentiation of the spectral bands on the detectors can also be implemented by using, for example, a reflection grating, or further by any other way known as such. Thus, the term "spectrometer" must, in this context, be understood to refer to all such optical devices, by which it is possible to separate the desired spectral bands corresponding to $CO_2$, CO, HC and the reference signal shown in FIG. 203 from the measuring beam 50 on different detectors in a desired manner. The spectrometer 60 used can also be a so-called FTIR spectrometer based on the fast Fourier transform.

The Implementation of the NO Measurement

In the following, we shall describe the solution for measuring the absorption and reference signal for NO according to the invention, based on correlation techniques, with reference to FIGS. 4 to 8.

Figure 4:
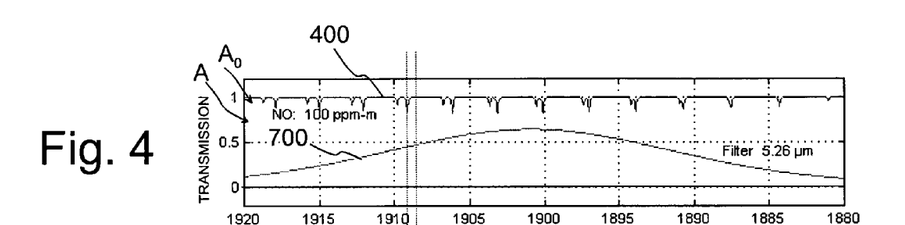
FIGS. 4 to 6 illustrate, in principle, NO measurement according to the invention by means of spectra.

In the wavelength range of 5.26 μm, the absorption spectrum of NO consists of spectral lines recurring at regular, substantially constant wavelength intervals according to the curve 400 in FIG. 4. When measuring the absorption caused by NO in a wide wavelength band, for example by means of a band pass filter with a transmission according to the curve 700 in FIG. 4, the sensitivity of such conventional measurement does not become very good, due to the narrowness of the spectral lines of NO in relation to the whole width of the measuring band.

The aforementioned problem, known as such from the absorption spectroscopy to anyone skilled in the art, can be better understood by means of the following example.

In a situation, in which the NO concentration of the gas plume to be measured would be zero, the measuring result is a reference signal which corresponds to the area (indicated with $A_0$) left below the curve 400 in FIG. 4 when there are no absorption peaks caused by NO in the curve 400 (in other words, the curve 400 is a horizontal line). In a situation, in which the NO concentration is 100 ppm-m as shown in FIG. 4, the measuring result is a corresponding surface left below the curve 400 (indicated with A). However, the difference here is that the spectral peaks of NO are now included, reducing said area. Consequently, the transmission of NO is now determined by means of the signals corresponding to the ratio of the areas $A/A_0$. Since the ratio $A/A_0$ is, in this situation, the ratio between two almost equal numbers, the measuring accuracy will thus become poor; in other words, the ratio $A/A_0$ is only slightly changed with a change in the NO concentration, because A is changed only slightly. In practice, the reference signal should be determined as precisely at the same time with the absorption signal as possible; therefore, the reference signal must be measured at such an adjacent wavelength band corresponding to the adsorption band of NO, at which NO is substantially not absorbent. This will further reduce the measuring accuracy, because in this case the background caused by water vapour, which is always present to some extent in the gas plume to be measured and/or in the ambient air, is not precisely the same in the reference band and in the absorption measuring band; in other words, the absorption caused by water vapour does not remain precisely constant as a function of the wavelength.

According to the present invention, said problem is solved by making the NO measurement by using, as the filter determining the measuring bands, such an optical filter or filter arrangement, in which the penetration of said filter means as a function of the wavelength correlates with the comb-like structure of the spectral lines of the absorption spectrum present in the vicinity of the 5.25 μm wavelength of NO.

According to the invention, said filter means used is preferably either an NO gas cell filter or a Fabry-Perot comb filter. It is thus possible to measure the reference signal and the absorption signal precisely at the same time, and particularly in the case of the Fabry-Perot comb filter, the sensitivity of the measurement is significantly improved, thanks to the narrow measuring band. Furthermore, since the absorption signal is measured at wavelengths which are in the direct vicinity of the wavelengths used in the measurement of the reference signal, the background absorption caused by impurities etc. and particularly water vapour contained in the air and/or in the exhaust gas plume is also more precisely taken into account.

Figure 5:
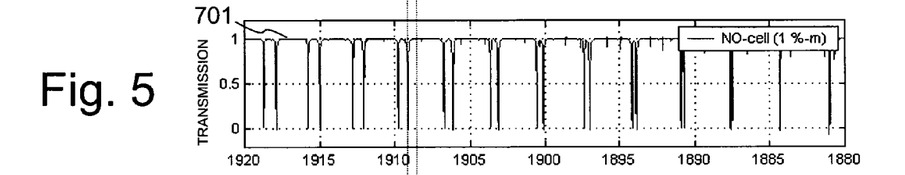

FIG. 5 shows the transmission spectrum of an NO gas cell filter in a situation, in which the filter contains a high concentration of NO gas, for example 1%-m. In this case, the NO cell filter passes practically no light at the wavelengths of the spectral lines of NO; in other words, the transmission at the spectral lines of NO is substantially zero, as shown in FIG. 5.

Figure 7:
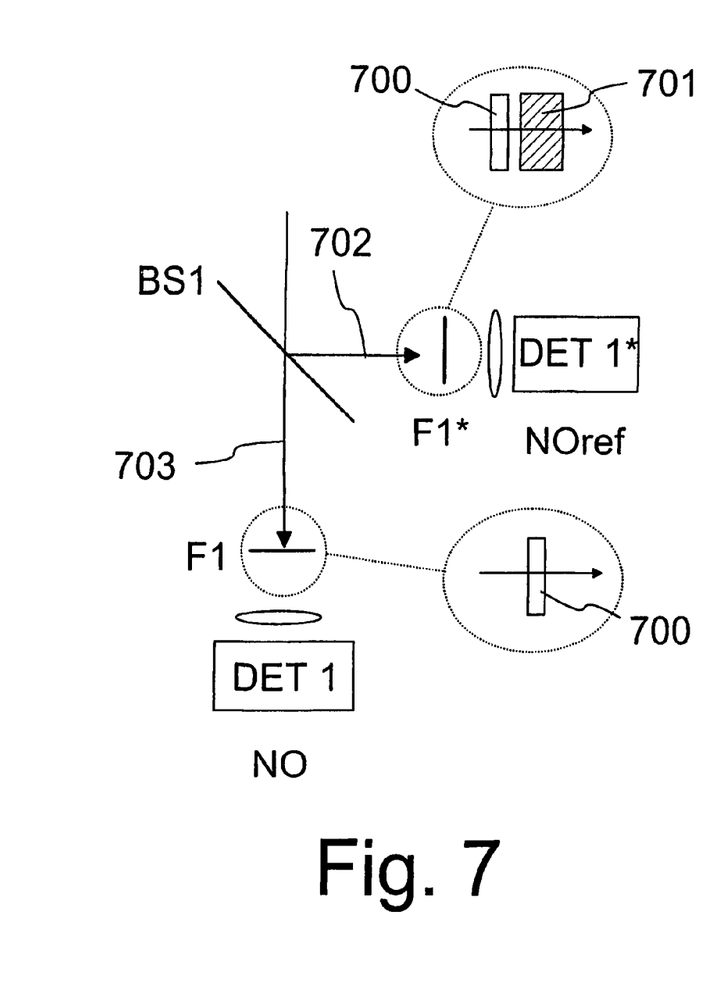
FIG. 7 illustrates, in principle, an embodiment of a detector section of a spectrometer for measuring NO, using an NO cell filter.

FIG. 7 shows an optical arrangement for measuring the reference and absorption signals of NO utilizing an NO gas cell filter according to the invention. The light coming to the NO measuring section of the spectrometer 60 is split with a beam splitter 1 into reference and measuring channels 702, 703 in such a way that light is directed to each of said channels at pass bands with substantially equal width in wavelength. The width of the pass band covers at least partly or totally the wavelength range, in which the NO line spectrum is present in the vicinity of 5.26 μm in the IR range. With respect to the intensity, the splitting ratio of the beam splitter BS1 can, if necessary, differ from the splitting ratio 50/50, to achieve an optimal signal level for the detectors DET1* and DET1. The filter F1* of the reference measuring channel 702 comprises a combination of a wide band pass filter 700 (see FIG. 4, curve 700) and an NO gas cell filter 701. Thus, the reference signal measured by the detector DET1* is independent of the NO concentration of the object to be measured. In a corresponding manner, the filter F1 of the measuring channel 702 comprises only a wide band pass filter 700, which has preferably similar transmission properties as the filter used for the reference channel 702. Now, the difference between the reference signal measured by the reference channel 702 and the absorption signal measured by the measuring channel 703 is changed in proportion to the NO concentration of the object to be measured.

It will be obvious for a person skilled in the art that the filters 700, placed separately in the reference channel 702 and in the band pass channel 703 in FIG. 7 can, if desired, be replaced by placing alternatively one such filter before the beam splitter BS1. Furthermore, it will be obvious for a person skilled in the art that it is possible, if necessary, to install a so-called dummy filter in the measuring channel 703, to bring the optical properties of the reference channel 703 and the band pass channel 703 to correspond to each other (except for the absorption of NO).

Figure 8:
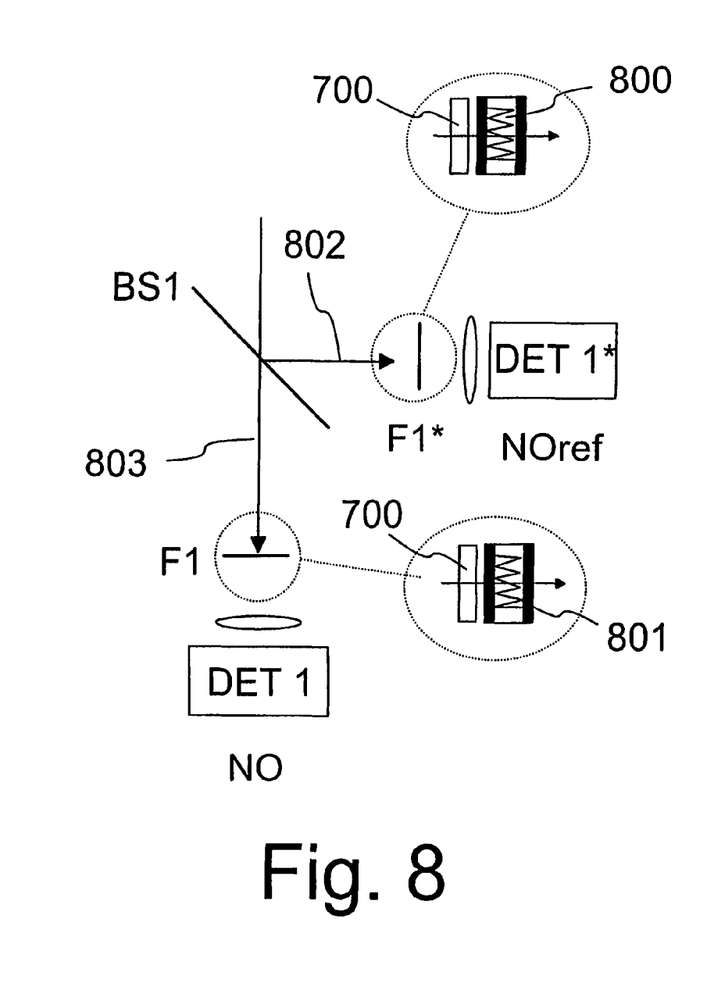
FIG. 8 illustrates, in principle, an embodiment of a detector section of a spectrometer for measuring NO, using Fabry-Perot comb filters.

FIG. 8 shows an optical arrangement according to the invention, for measuring the reference and absorption signals of NO by utilizing Fabry-Perot filters (below, briefly FP filter).

The operation of the FP filter is based on an optical cavity formed between two end mirrors which are precisely aligned with each other and are partially light-transmitting. Depending on the wavelength of the light guided through the end mirror into the cavity, the light is subjected to either constructive or destructive interference in the cavity. In the case of destructive interference, the light is not transmitted through the cavity, but in the case of constructive interference, the cavity is substantially transparent. The principles of operation of the FP cavity and optical filters based on it are well known as such in spectroscopy, and they will therefore not need to be discussed in more detail in this context.

According to the invention, for the measurement of the reference and absorption signals, so-called FR comb filters 800, 801 are placed in the reference and measuring channels 802, 803, respectively. To limit the measuring wavelength band, the reference and measuring channels 802, 803 each also comprise wide band pass filters 700, whose transmission complies substantially with the curve 700 of FIG. 4. In a corresponding way, in the situation of FIG. 8, said band pass filters 700 can also be alternatively replaced by one corresponding filter placed before the beam splitter BS1.

Figure 6:
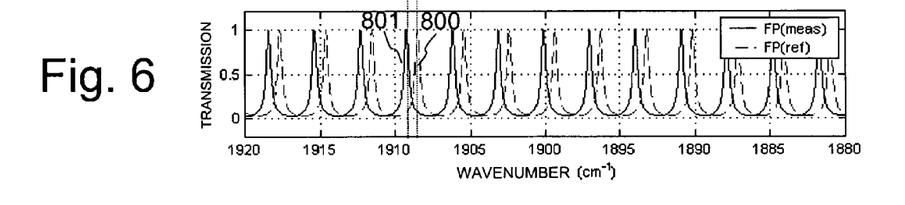

The filter F1* of the reference channel 802 comprises an FP comb filter 800, whose transmission curve is shown as curve 800 in FIG. 6. The wavelength ranges recurring in the curve 800 of FIG. 6, i.e. the comb transmission peaks at which the FP comb filter 800 transmits light, are arranged, by suitable tuning of the FP cavity, to recur at intervals corresponding to the gaps of the NO spectral peaks in such a way that the transmission ranges of the FP comb filter occur between the spectral peaks of NO.

The FP comb filter can be tuned in a known way by altering the distance between the end mirrors of the cavity and/or by changing the angle of incidence of light in relation to the FP comb filter, to affect the so-called free spectral range of the cavity and the distances between the transmission peaks in the transmission spectrum of the FP filter.

In a corresponding manner, the filter F1 of the measuring channel 803 comprises an FP comb filter 801, whose transmission curve is shown as curve 801 in FIG. 6. The FP comb filter 801 of the measuring channel is tuned so that the transmission ranges of the filter 801 overlap with the peaks of the NO spectrum.

Now, the difference between the reference signal measured by the reference channel 802 and the absorption signal measured by the measuring channel 803 is proportional to the NO concentration of the object to be measured. With the measurement, a good sensitivity is achieved for the NO concentration, because the transmission wavelengths and bands of the FP comb filter 801 of the measuring channel 803 correspond to the wavelengths and width of the NO absorption spectral lines; in other words, a change in the absorption caused by NO will strongly affect the quantity of light transmitted to the detector DET1. Furthermore, since the reference channel 802 is in the direct vicinity of the wavelengths used in the measurement of the absorption signal of the reference signal, the background absorption caused by water vapour is precisely taken into account.

In an advantageous embodiment of the NO measurement according to the invention, the tuning of the FP comb filters 800 and 801 is fixed; in other words, the effective distance between the end mirrors of the cavity is arranged to be constant. Said effective distance between the end mirrors, experienced by the beam of light passing the FP cavity, can be affected, in addition to the movement of the mirrors, by inclining the FP comb filter in relation to the optical axis of the beam of light passing through it. In other words, by selecting the initial distance between the mirrors of the FP cavity in a suitable way so that the transmission of the cavity recurs at intervals of the NO spectral lines, it is possible to finetune both FP comb filters 800 and 801 by altering their angle with respect to the incident beam of light. The FP comb filter 800 is tuned so that its peaks come next to the NO absorption spectral lines, and the FP comb filter 801 is tuned so that its peaks overlap with the NO absorption spectral lines.

By this arrangement, it is possible to measure the reference and absorption signals simultaneously by the optical arrangement of FIG. 8, in which separate FP comb filters 800, 801, tuned in a different, stationary manner, and separate detectors DET1*, DET1 are placed in both the reference channel 802 and the measuring channel 801.

The FP cavities in the FP comb filters 800 and 801 can be implemented by using either air (or another suitable gas) or a solid transparent material as a medium between the end mirrors. Because the operation of the FP cavity is based on interference, even slight changes in the distance between the end mirrors will affect the transmission of the cavity. Consequently, it is advantageous to use a ring, or the like, made of a material with a low thermal expansion coefficient (e.g. Zerodur®) as a spacer between the end mirrors in an FP cavity with an air medium. In a corresponding manner, an FP cavity with a solid medium, it is advantageous to use as the optical medium a material whose thermal expansion coefficient is substantially equal to its thermal refractivity coefficient in its absolute value but has a different sign. Such a material is, for example, barium fluoride ($BaF_2$), in which the change in the optical distance caused by thermal expansion is compensated for by the change in the refractive coefficient of the material.

The NO measurement according to the invention can also be implemented by a so-called scanning FP technique. Thus, only one FP comb filter with adjustable tuning is used instead of two separate FP comb filters with fixed tuning placed in the reference and measuring channels 802, 803. The adjustment of the tuning of the FP comb filter can be implemented in a way known as such, for example by a solution in which the distance between the end mirrors of the FP cavity is adjusted by piezo crystals. Thanks to this, fast temporal scanning of the transmission of the FP comb filter becomes possible between the situations shown by the curves 800 and 801 in FIG. 6, wherein either the reference signal or the absorption signal can be detected by the detector at given moments of time. If the scanning rate is, for example, in the order of hundreds of herzes or kiloherzes, the reference and absorption signals can be determined in such a way that the time difference between the measuring of the reference signal and the measuring of the absorption signal is so small that, in practice, they correspond to measurements made at the same time, wherein the properties of the object to be measured do not change in this time. The use of a scanning FP comb filter has the advantage that no separate reference and measuring channels will be needed to measure the NO concentration, wherein the number of components in the apparatus is reduced.

Instead of using an NO gas cell filter or an FP comb filter, it is also possible to use any other filtering means whose transmission as a function of the wavelength correlates with the comb-like structure of the spectral lines of the absorption spectrum present in the vicinity of the 5.25 µm wavelength of NO. Such a filter can also be implemented by using, for example, diffractive optical gratings.

Figure 9:
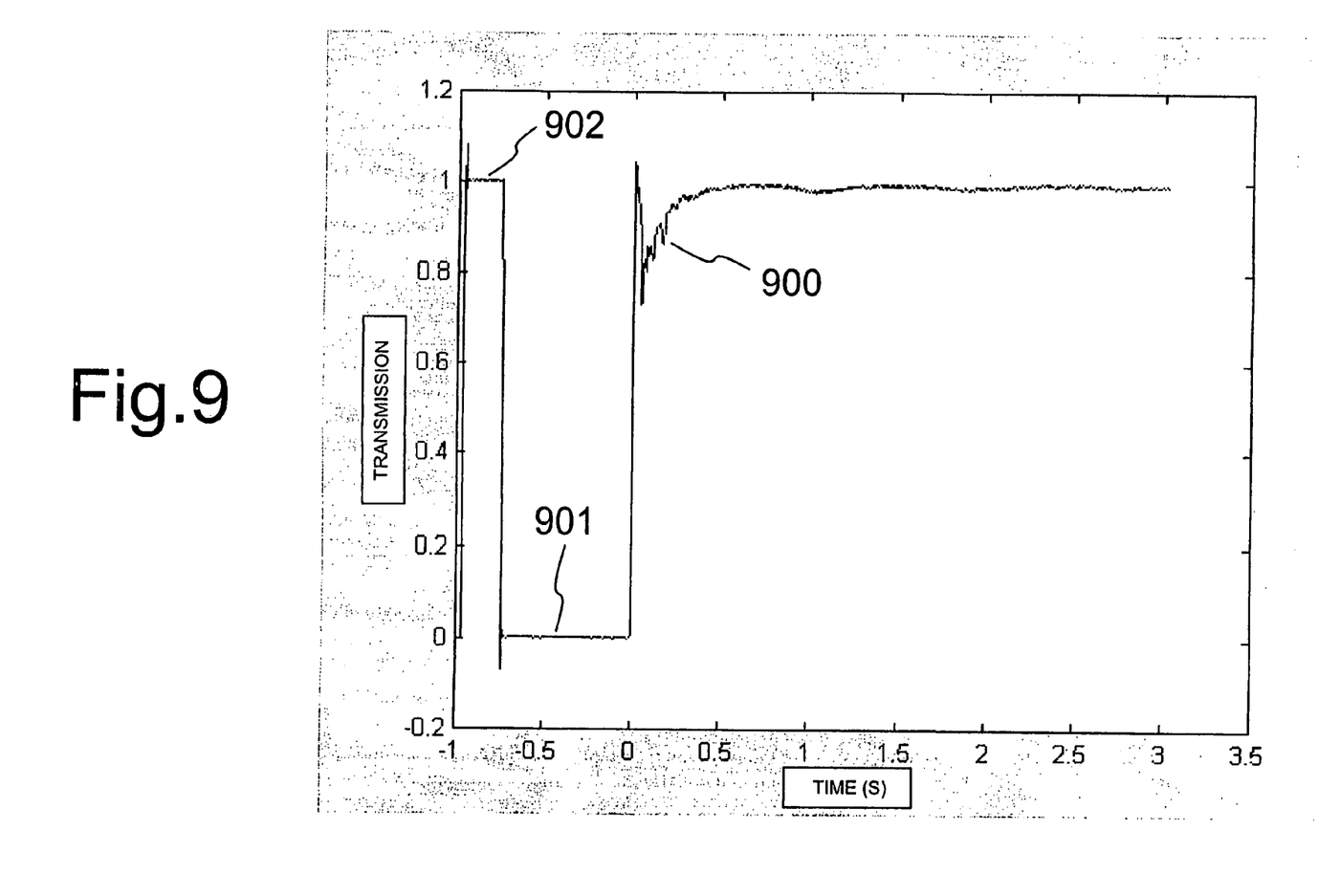
FIG. 9 illustrates, in principle, the temporal behaviour of absorption caused by $CO_2$ in a measuring situation.

Furthermore, FIG. 9 illustrates, in principle, the temporal behaviour of the absorption caused by $CO_2$ in a measuring situation when the vehicle passes the measuring beam 50. In the curve of FIG. 9, in the section indicated with reference number 901, the vehicle passes the measuring beam 50 and prevents the entry of the measuring beam at the spectrometer 60. In the section indicated with the reference number 900, the absorption caused by the exhaust gas plume 40 of the vehicle in the measuring beam 50, in this case the absorption of $CO_2$, is detected for a short time (<0.5 s) during a period which starts when the vehicle has moved away from the measuring beam 50 and which ends when the exhaust gas plume 40 is dissolved by the effect of air turbulence caused by the vehicle, wind, etc. On the basis of FIG. 9, it is obvious that the optical measurements to determine the gas concentrations of the exhaust gas plume 40 (blocks 201–206 in FIG. 2) must be made substantially simultaneously, wherein the composition and properties of the gas plume 40 do not have time to change during the measurement.

If the measurements corresponding to the blocks 201–206 in FIG. 2 are also made immediately before the vehicle enters the measuring point, i.e. in the section indicated with the reference numeral 902 in FIG. 9, it can be made sure that the vehicle in question really caused the emissions measured at the section indicated with the reference numeral 900. If the emissions measured immediately before the entry of the vehicle at the measuring point are different from the normal prevailing quality of air, the measuring result can be marked as unreliable. Such a situation may occur, for example, when two vehicles drive closely one after the other and the emissions of the first vehicle, which are considerably larger than normal, do not have time to dissolve and dilute and are thus shown also in the measuring result of the following vehicle.

It is, of course, obvious for anyone skilled in the art that by combining, in different ways, the methods, modes of operation and device structures presented above in connection with different embodiments of the invention, it is possible to provide various embodiments of the invention in accordance with the spirit of the invention. Therefore, the above-presented examples must not be interpreted as restrictive to the invention, but the embodiments of the invention can be freely varied within the scope of the inventive features presented in the claims hereinbelow.

For example, it is possible that in the future, regulated emissions from vehicles are also determined to include other gases, such as benzene, 1,3-butadiene or $N_2O$. The solutions according to the invention can also be applied in the measurement of such gases.

Furthermore, it will be obvious for a person skilled in the art that in the blocks 201–206 of FIG. 2, it will not be quite necessary in all embodiments of the invention to determine the transmission values precisely in the way defined in connection with Formula 1, but in some situations, it is possible, in block 208, to proportion values of the "raw" signal, which are directly proportional to the transmission, with each other without substantially reducing the accuracy of the measurement.

The invention claimed is:

1. A method for determining and monitoring exhaust gas emissions of a moving vehicle or a corresponding object by a remote measuring technique, the method comprising:
   forming a measuring beam of infrared radiation, which measuring beam is directed once or several times through an exhaust gas plume emitted by the vehicle,
   determining, by means of the measuring beam, an optical measuring value for carbon dioxide said measuring value indicating the optical absorption caused by carbon dioxide contained in the exhaust gas plume in the measuring beam,
   determining, by means of the measuring beam, an optical measuring value for one or more actual emission gases each, said measuring value indicating the absorption caused by said emission gas contained in the exhaust gas plume in the measuring beam, proportioning the optical measuring values determined for the actual emission gases each with the optical measuring value determined for carbon dioxide and solving, by means of an estimate determined for the carbon dioxide concentration of the exhaust gas plume, the concentrations of the actual emission gases in the exhaust gas plume by means of said optical measuring values, wherein for the more precise determination of the actual emission gases in the exhaust gas plume, the method further comprising:

identifying the model and/or type of the vehicle under examination, determining the driving situation of said vehicle at the moment of measurement, and further forming a calculatory vehicle model for determining a case-specific estimate for the carbon dioxide concentration of the exhaust gas plume depending on the vehicle in question and its driving situation.

2. The method according to claim 1, wherein the optical measuring value determined for carbon dioxide and the case-specific concentration estimate determined for carbon dioxide by means of the calculatory vehicle model are used to determine the effective absorption length of the measuring beam in the exhaust gas plume, which is further used to determine the concentrations of the actual emission gases.

3. The method according to claim 1, wherein the optical measuring value, such as transmission, are determined for all the measured gases substantially at the same time and at the same point in the exhaust gas plume.

4. The method according to claim 1, wherein the vehicle is identified on the basis of the registration plate of the vehicle.

5. The method according to claim 4, wherein the data contained in the registration plate of the vehicle are used to retrieve the exact type and/or model data of the vehicle from a register database.

6. The method according to claim 5, wherein the type and/or model data of the vehicle are used to retrieve more detailed information about the vehicle model in question.

7. The method according to claim 6, wherein said more detailed information about the vehicle model in question comprises at least one of the following: dead weight, engine type, and properties of the transmission apparatus.

8. The method according to claim 1, wherein to determine the driving situation at the moment of measuring the vehicle, the speed and/or acceleration of the vehicle are determined.

9. The method according to claim 8, wherein the total weight of the vehicle and/or the weather conditions at the measurement site and time, and/or the profile of the surface of the road in the driving direction at the measurement site, and/or the roughness of the surface of the road prevailing at the measurement site and time are also measured to determine the driving situation at the moment of the measurement of the vehicle.

10. The method according to claim 1, wherein the optical measuring value for nitrogen oxide is determined in the infrared range in the vicinity of the wavelength of 5.26 μm by using, for wavelength filtering or as part of the wavelength filtering in reference and/or measuring channels intended for NO, a filtering means whose transmission as a function of the wavelength correlates with the comb-like structure of the spectral lines of the absorption spectrum present in the vicinity of 5.25 μm of nitrogen oxide.

11. The method according to claim 10, wherein in each of the reference and measuring channels intended for NO, Fabry-Perot comb filters are used for the wavelength filtering or as part of the wavelength filtering.

12. The method according to claim 10, wherein in the measuring channel intended for NO, a scanning Fabry-Perot comb filter is used for the wavelength filtering or as part of the wavelength filtering.

13. The method according to claim 10, wherein in the reference channel intended for NO, an NO gas cell filter is used for the wavelength filtering or as part of the wavelength filtering, and, if necessary, a corresponding so-called dummy filter is used in the measuring channel, to balance the optical properties of said channels.

14. The method according to claim 1, wherein a calculatory vehicle model is used to determine an estimate for the fuel consumption of the vehicle at the moment of measuring, which is used to convert the measured emission values to emission coefficients in the form of g/km and/or g/s and/or g/kWh.

15. The method according to claim 1, wherein measurements are made for benzene and/or 1,3-butadiene and/or $N_2O$.

16. A measuring system for determining and monitoring exhaust gas emissions from a moving vehicle or a corresponding object by a remote technique, the system comprising:

means for forming a measuring beam of infrared radiation and for directing the measuring beam once or several times through an exhaust gas plume emitted by the vehicle, means for determining, by means of the measuring beam, an optical measuring value for carbon dioxide said measuring value indicating the optical absorption caused by carbon dioxide contained in the exhaust gas plume in the measuring beam, means for determining, by means of the measuring beam, an optical measuring value for one or more actual emission gases each, said measuring value indicating the absorption caused by said emission gas contained in the exhaust gas plume in the measuring beam, means for proportioning the optical measuring values determined for the actual emission gases to the optical measuring value determined for carbon dioxide, and means for solving the concentrations of the actual emission gases of the exhaust gas plume on the basis of the estimate determined for the carbon dioxide concentration of the exhaust gas plume and said optical measuring values, wherein for the more precise determination of the actual emission gases in the exhaust gas plume, the measuring system further comprising:

means for identifying the model andlor type of the vehicle under examination, means for determining the driving situation of the vehicle at the moment of measuring, and further means for forming a calculatory vehicle model for determining a case-specific estimate for the carbon dioxide concentration of the exhaust gas plume depending on the vehicle in question and its driving situation.

17. The measuring system according to claim 16, wherein the measuring system comprises means for determining the effective absorption length of the measuring beam in the exhaust gas plume by using an optical measuring value determined for carbon dioxide and a case-specific concentration estimate determined for carbon dioxide on the basis of a calculatory vehicle model, as well as means for determining the concentrations of the actual emission gases by means of said effective absorption length.

18. The measuring system according to claim 16, wherein the measuring system comprises means for determining said optical measuring values for all the measured gases substantially at the same time and at the same point in the exhaust gas plume.

19. The measuring system according to claim 16, wherein the measuring system comprises means for identifying the vehicle on the basis of the registration plate of the vehicle.

20. The measuring system according to claim 19, wherein the measuring system comprises means for retrieving the exact type and/or model data of the vehicle from a register database by means of the data contained in the registration plate of the vehicle.

21. The measuring system according to claim 20, wherein the measuring system comprises means for retrieving more detailed information about the vehicle model in question by means of said type and/or model data of the vehicle from a separate type database.

22. The measuring system according to claim 21, wherein said more detailed information about the vehicle model in question comprises at least one of the following: dead weight, engine type, and properties of the transmission apparatus.

23. The measuring system according to claim 16, wherein the measuring system comprises means for determining the speed and/or acceleration of the vehicle in the driving situation at the moment of measuring.

24. The method according to claim 23, wherein the measuring system also comprises means for measuring the total weight of the vehicle and/or the weather conditions at the measurement site and time, and/or the profile of the surface of the road in the driving direction at the measurement site, and/or the roughness of the surface of the road prevailing at the measurement site and time.

25. The measuring system according to claim 16, wherein the measuring system comprises means for determining the optical measuring value for nitrogen oxide at the infrared range in the vicinity of the wavelength of 5.26 µm in such a way that, for wavelength filtering or as part of the wavelength filtering in reference and/or measuring channels intended for NO, a filtering means is used, whose transmission as a function of the wavelength correlates with the comb-like structure of the spectral lines of the absorption spectrum present in the vicinity of 5.25 µm of nitrogen oxide.

26. The measuring system according to claim 25, wherein the measuring system comprises, in each of the reference and measuring channels intended for NO, a Fabry-Perot comb filter with substantially fixed tuning for the wavelength filtering or as part of the wavelength filtering.

27. The measuring system according to claim 25, wherein the measuring system comprises, in the measuring channel intended for NO, a scanning Fabry-Perot comb filter for the wavelength filtering or as part of the wavelength filtering.

28. The measuring system according to claim 25, wherein the measuring system comprises, in the reference channel intended for NO, an NO gas cell filter for the wavelength filtering or as part of the wavelength filtering, and, if necessary, a corresponding so-called dummy filter in the measuring channel, to balance the optical properties of said channels.

29. The measuring system according to claim 16, wherein the measuring system comprises means for determining, by means of a calculatory vehicle model, an estimate for the fuel consumption of the vehicle under examination at the moment of measuring, and means for indicating the measured emission values as emission coefficients in the form of g/km and/or g/s and/or g/kWh by means of said estimate for the fuel consumption.

30. The measuring system according to claim 16, wherein the measuring system comprises means for setting up a data transmission connection and for data transmission between the measuring system and one or more external systems.

31. The method according to claim 16, wherein the measuring system also comprises means for taking measurements for benzene and/or 1,3-butadiene and/or $N_2O$.

* * * * *